United States Patent [19]

Schaffner et al.

[11] Patent Number: 4,983,518

[45] Date of Patent: Jan. 8, 1991

[54] EUKARYOTIC EXPRESSION VECTORS WITH MULTIMERIC ENHANCER SEGMENTS, A PROCESS FOR THE PREPARATION THEREOF AND THE USE THEREOF

[75] Inventors: Walter Schaffner, Weiningen, Switzerland; Nils G. Westin, Upsala, Sweden

[73] Assignee: Boehringer Mannheim GmbH, Mannheim, Fed. Rep. of Germany

[21] Appl. No.: 213,091

[22] Filed: Jun. 29, 1988

[30] Foreign Application Priority Data

Jul. 11, 1987 [DE] Fed. Rep. of Germany ....... 3723075

[51] Int. Cl.$^5$ .................. C12N 15/67; C12N 15/85
[52] U.S. Cl. .................................. 435/69.1; 435/320
[58] Field of Search ............... 435/69.1, 70.1, 70.3, 435/172.1, 172.3, 235, 252.3, 320; 935/6, 8, 22, 33, 34

[56] References Cited

PUBLICATIONS

Zenke, M. et al., Embo J., 5(2), 387–397 (1986).
Searle et al., (1985) Mol Cell Biol, 5:1480–1489.
Kumar et al., (1986) PNAS, 83: 3199–3203.
Veldman et al., (1985) Mol Cell Biol, 5:649–658.
Toohey et al., (1986) Mol Cell Biol, 6:4526–4538.
Mann et al., (1983) Cell 33: 153–159.
Miller et al., (1984) Science, 225:993–998.

Primary Examiner—Richard A. Schwartz
Attorney, Agent, or Firm—Felfe & Lynch

[57] ABSTRACT

The present invention provides a eukaryotic expression vector containing a gene to be expressed and a TATA box, whereby, 1–200 bp base pair (bp) upstream (5') of the TATA box, there is a first multimeric enhancer segment and 1–100 bp below (3') the gene to be expressed there is provided a second multimeric enhancer segment. The present invention also provides a process for the preparation of this expression vector. Furthermore, the present invention is concerned with the use of this expression vector.

9 Claims, 2 Drawing Sheets

EUKARYOTIC EXPRESSION VECTORS WITH MULTIMERIC ENHANCER SEGMENTS, A PROCESS FOR THE PREPARATION THEREOF AND THE USE THEREOF

The present invention is directed to a eukaryotic expression vector containing multimer enhancer elements, a process for the preparation thereof, and a method for expression of proteins in mammalian cells transfected by said vectors.

Expression of proteins in mammalian cells (hereafter referred to as "heterologous proteins"), is of interest and has become important in many areas, including diagnostics and therapeutics.

Heterologous proteins can be expressed in mammalian cells and in prokaryotic cells. When expressed in mammalian cells, this is accomplished via transfecting the chosen host cell with a vector. Generally the vector employed contains elements of a virus. Thus, vectors containing elements of bovine papilloma virus (Proc. Natl. Acad. Sci. USA 81: 5086-5090 (1984); simian virus 40 (SV40) (Proc. Natl. Acad. Sci. USA 82: 3644-3648 (1985); retroviruses (DNA 4: 23-31 (1985); and adenovirus (Proc. Natl. Acad. Sci. 82: 3567-3571 (1985). For the most part, these vectors are based on the structure of a DNA-virus, and also contain a gene coding for the protein to be expressed. Additional elements of the vector may include, e.g., a resistance gene or "marker" which serves to "select" transformed cells; a promotor; an origin of DNA replication or "ori" sequence; and activating sequences of DNA, referred to as "enhancer elements". See, in this regard Science 209: 1422-1427 (1980).

The eukaryotic vectors produced in the fashion generally described, supra, do transform some mammalian cells. Production of heterologous protein from the transformed cell, however, is in very low yields as compared to expression of heterologous proteins in prokaryotic transformants. With respect to the limited number of mammalian cell types which express heterologous protein following transformation, see, e.g., DNA 3: 297-308 (1984); Mol. and Cell Biol. 4: 166-172 (19840 (Chinese Hamster Ovary or "CHO" cells); and Proc. Natl. Acad. Sci. 82: 3567-3571 (1985) (HeLa cells transformed by adenovirus vectors).

When transformation of a prokaryote, such as bacteria takes place, the vector is cloned into a bacterial plasmid. The resulting plasmid frequently contain enhancer elements. These enhancer elements are mostly arranged upstream (5') of the gene to be expressed, either outside or overlapping with the promotor sequence. Enhancer elements also manifest their activity in a position within or also downstream (3') of the transcription unit. The length of these elements is usually from 70 to 300 bp (SV40 enhancer, polyoma virus enhancer, Nucl. Acids Res., 10, 7965-7976/1982) but substantially longer enhancer elements have also been found (Cell, 41, 521-530/1985, PNAS, 82, 8325-8329/1985). The enhancer elements can stimulate transcription in eukaryotic cells and are therefore, of particular interest. This stimulating action is largely independent of the position and the orientation of the enhancer element in the vector (Cell, 27, 29-308/1981).

Enhancer elements are found in eukaryotic viruses (for example SV40, polyoma virus, BVP, cytomegalovirus, MSV and HIV), as well as in eukaryotic genes, for example the genes for immunoglobulin, interferon, chymotrypsin and insulin. In the case of SV40, most of the enhancer activity is localized in a 72 bp long repeat which is present upstream (5') of the transcription start (Cell, 27, 299-308/1981). This 72 bp repeat contains a core sequence which contributes substantially to the enhancer function (Science) 219, 626-631/1983). However, an isolated core sequence is quite inactive (Genes Dev., 1, 65-73/1987). It functions well in the context of its natural neighbouring sequences (Cell, 39, 653-662/1984). However, even such extended enhancer sequents give an activity of at most 5% of that of the wild type (Mol. and Cell. Biol., 5, 649-658/1985). A substantial increase of the expression takes place when the enhancer elements are multimerised. Thus, a segment of 26 bp of the polyoma virus enhancer which was contained in the vector in 5-7 copies, yielded even a slightly higher transcription rate than the wild type enhancer (Mol. and Cell. Biol , 5, 649-658/1985).

However, in comparison with the expression of foreign genes in prokaryotes, the expression in eukaryotes, with the use of the known promotors, proceeds with only comparatively low yields.

Therefore, it is an object of the present invention to provide an improved expression system which ensures the expression of foreign genes in mammalian cells at a high level.

Thus, according to the present invention, there is provided a eukaryotic expression vector that contains a gene to be expressed and a TATA box, wherein, 1-200 base pairs (bp) upstream (5') of the TATA box, there is provided a first multimeric enhancer segment and 1-1000 bp below (3') the gene to be expressed there is provided a second multimeric enhancer segment.

Surprisingly, we have found that, with the expression vectors according to the present invention, a substantially higher expression can be achieved than with all of the previously known systems. This is all the more surprising since with vectors which contain only the first or only the second multimeric enhancer element, no particularly high expression could be observed.

The multimeric enhancer segments consists of 3-30 individual enhancer segments arranged behind one another. Preferably, the first multimeric segment is present in 3-10 copies and the second multimeric segment is present in 5-30 copies. Multimers are especially preferably used as tandem copies ("direct repeats") enhancer segment The 3' end of the first element is arranged 1-200 base pairs upstream (5') of the TATA box and preferably 8-20 base pairs upstream of the TATA box. The 5' end of the second multimeric enhancer segment is arranged 1-1000 bp and preferably 10-300 bp downstream (3') of the gene to be expressed.

The individual enhancer segments have a length of 15-60 bp and consist of at least one and preferably 1-7 enhancer sequence motifs but, besides the sequence motifs, can also contain flanking neighbouring sequences. The neighbouring sequences can correspond to the neighbouring sequences of the sequence motifs occurring in natural enhancers but can also be any other desired sequences.

The term enhancer sequence motifs refers to those sequences of an enhancer which are essential for the enhancer action and, consequently, can be regarded as being the most relevant sequences of the enhancer. The length of these enhancer sequence motifs is usually from 8 to 18 bp. These sequence motifs frequently show homology to the enhancers from other viruses and cellular genes.

Examples of preferred enhancer sequence motifs are (N is any desired nucleotide):

(E1a core enhancer, Cell, 33, 695–703/1983)

(sequence homologous to immunoglobulin and viral enhancers, Science, 219, 626–631/1983)
TGTGGTAAG (MSV, PNAS, 79, 6453/1982)
GTGTGGAAAG (Science, 219, 626–631/1983)
TGGTTG (BPV, Cell, 18, 963/1979)
GTGTGGTTT (Py(F101), Nucleic Acids Res., 9, 6251/1981)
ATGCAAATNA (Nature, 310, 71–74/1986)
TNATTTGCAT (IgH enhancer, Banerji et al., Cell. 33, 729–740/1983)
TCAAGATGGC, AGCAGCTGGC, GICATGTGGC, ACCACCGGGT (Ephrussi motifs of the mouse IgH enhancer, Science, 227, 134–140/1983).

It is particularly advantageous to use enhancer sequence motifs of cellular genes (for example of the human IgH enhancer, Nature, 306, 806–809/1983).

In this way, the cell culture can be kept free from viral elements.

An especially preferred enhancer sequence motif is the MREwt oligonucleotide of the metallothionein enhancer:

Eight tandem copies of this enhancer sequence motif can be cut out, for example from the 4×MREwt/8×-MREwt plasmid (DSM 4098P) with EcoRI or XhoI.

The present invention also provides a process for the preparation of an expression vector according to the present invention, where by, according to known standard procedures of gene technology, at first multimeric enhancer segment is incorporated 1–200 bp and preferably 8–20 bp (5') of the, TATA box and a second multimer enhancer segment is incorporated 1–1000 bp and preferably 10–300 bp (3') of the gene to be expressed.

As vectors, there can thereby be used the vectors usually employed for mammalian cells, for example the vectors mentioned above.

If the polymerized enhancer segments have appropriate terminal sequences, they can be ligated directly into the vector. In other cases, compatible ends for the ligation must be produced first. This is achieved by filling protruding ends with Klenow polymerase or T4 polymerase, blunt ends thereby resulting for the ligation.

The present invention is also concerned with the use of an expression vector according to the present invention for the expression of proteins in mammalian cells. As mammalian cells, there can be used those cells in which the vectors according to the present invention are active. Examples thereof include vectors based on SV40 in CHO cells and vectors based on the plasmid pβ1E (DSM 4097P) in Hela cells.

If not stated otherwise the standard procedures of gene technology, such as cloning, DNA isolation and restriction, are carried out according to T. Maniatis et al., Molecular Cloning (1982), Cold Spring Harbor Laboratory, CSH, N.Y., 11724. Molecular biological reagents are used according to the manufacturer's instructions.

DETAILED DESCRIPTION OF PREFERRED EMBODIMENTS

EXAMPLE 1

Two complementary oligonucleotides (MREwt) of the sequences

containing a conserved MRE enhancer sequence motif and an Sp1 binding site, are mixed in equimolar amounts and multimerized as double-stranded DNA with the use of T4 ligase.

An introduction of linkers is unnecessary since the double-stranded oligonucleotides contain protruding complementary ends. After the ligation, the oligomers are labelled with $\alpha$-$_{32}$p dNTPS and the protruding ends are made blunt with T4 DNA polymerase.

The reaction products are subsequently size fractionated on a native polyacrylamide gel, a mixture of labelled DNA fragments being used simultaneously as molecular weight standards.

The 4- and 8-tandem copies of the oligonucleotide identified via autoradiography are cut out from the gel and eluted. The tetramer and the octamer are then, as described below, inserted into the plasmid pβ1E (DSM 4097P) upstream and downstream of the rabbit β-globin gene, respectively.

With these oligonucleotides the following plasmids are produced.

(a) Plasmid 4×MREwt (4 tandem copies upstream (5') of the rabbit β-globin gene)

The tetramer is inserted into the blunt-ended Hind III position in the vector pβ1E in position $-36$ of the rabbit β-globin gene. Apart from the TATA box, this plasmid contains no further β-globin gene promotor elements. In addition to the globin gene, the vector contains several kilobase pairs from the globin gene downstream neighbouring sequences.

(b) Plasmid 8×MREwt (8 tandem copies downstream of the β-globin gene)

The octamer is first ligated into the Eco RV site of the vector pUC 7/X (DSM 4177P) (which contains the multilinkers Eco RI, Xho I, Eco RV, Xho I and Eco RI integrated into pUC7). Subsequently, it is treated with Eco RI and the smaller fragment (200 bp) isolated by preparative agarose gel electrophoresis and inserted into the Eco RI site downstream (+2 kbp distance from the 5'end or 700 bp distance fro the 3' end of the β-globin gene) of the β-globin gene into the plasmid pβ1E.

(c) Plasmid 4×MREwt/8×MREwt (DSM 4098P) (this plasmid contains 4 tandem copies upstream and 8 tandem copies downstream of the β-globin gene)

Figure 1:
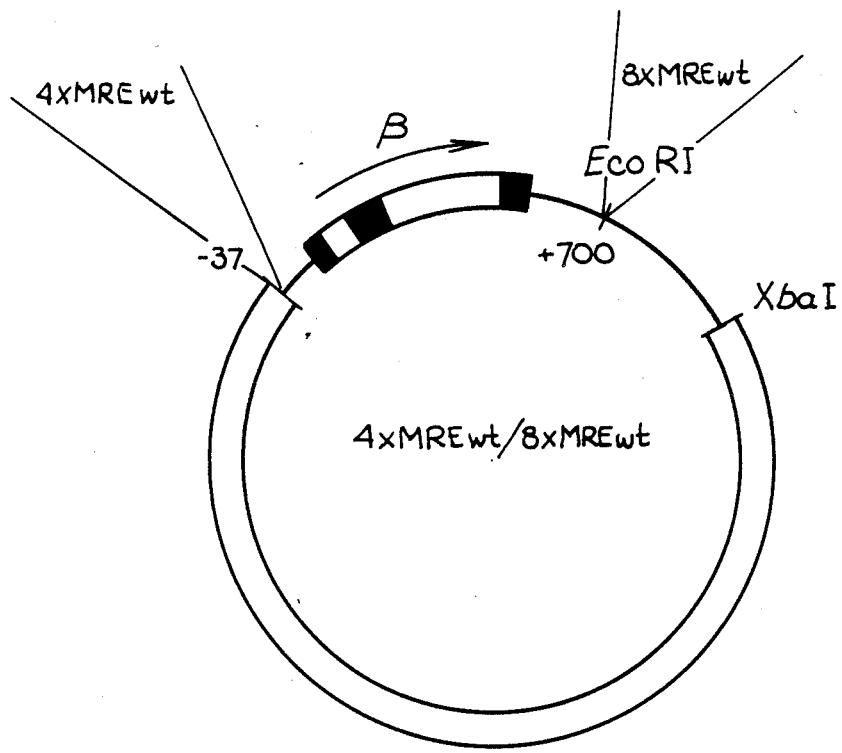
FIG. 1 is a plamid 4×MREwt/8×MREwt.
Figure 2:
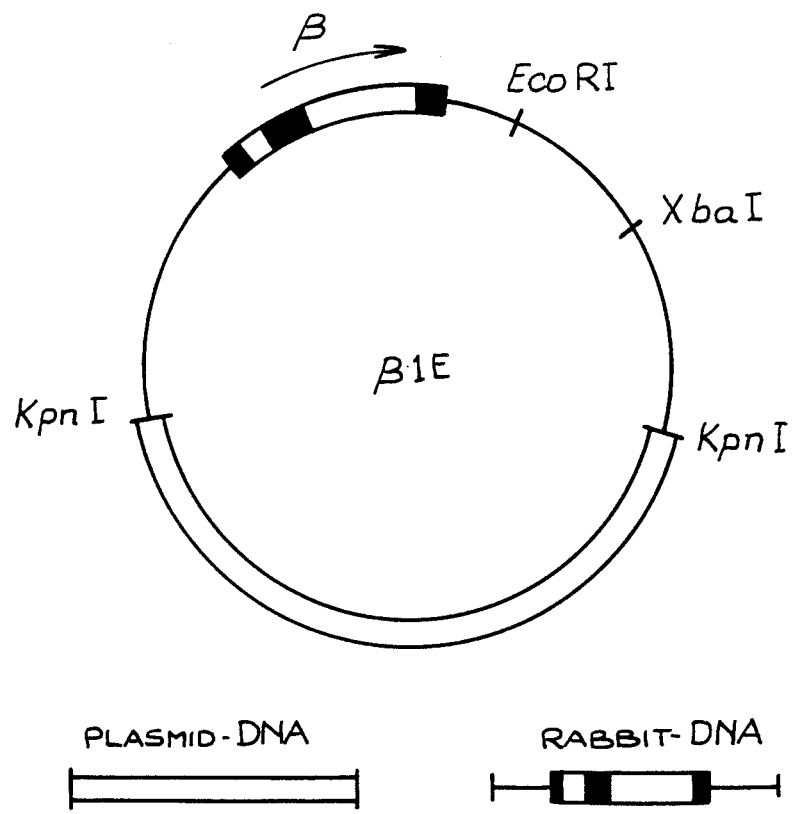
FIG. 2 is plasmid pβ1E.

The 0.5 kbp Eco RI/Bam HI fragment from the plasmid 4×MREwt and the 2.1 kbp Bam H/Xba I fragment from the plasmid 8×MREwt are ligated into the Eco RI/Xba I site of the vector M13mp18 and pUC 18, respectively (sequence: Gene, 33, 103–119/1985) (FIG. 1).

The plasmids are cloned into *Escherichia coli* HB 101 (DSM 1607) and are subsequently isolated.

EXAMPLE 2

Plasmid SV40 enhancer (plasmid which contains an SV40 enhancer element downstream (3') of the β-globin gene)

A 200 bp fragment of SV40 (Weber et al., Cell, 36, 983–995/1984), which corresponds to the nucleotides 95–294 of SV40, is provided on the 5'-side with an Xho I/Eco RI and on the 3'-side with an Xho I linker. From multiple tandem copies, an Eco RI fragment is excised and inserted directly into the Eco RI site of plasmid pβ1E.

EXAMPLE 3

Transfection of eukaryotic cells with the plasmids from Example 1 and 2

Hela cells (ATCC No. CCL2, adherent cells) are transfected according to the calcium phosphate transfection method as is described, for example, by Wigler et al. (Cell, 14, 725–731/1978) and by Weber et al. (Cell, 36, 983–992/1984) with the plasmids from Examples 1 and 2. For the determination of the transcription activity of the cells, the medium is removed by suction, and 10 ml. TBS (25 mmole/liter Tris-HCl, pH 7.4. 137 mmole/liter sodium chloride, 5 mmole/liter potassium chloride and 0.6 mmole/liter disodium hydrogen phosphate) are added and, after an incubation time of a few minutes at ambient temperature, again removed by suction. Subsequently, 4 ml. of 25% dimethyl sulphoxide (DMSO) in TBS are added, followed by incubation at ambient temperature for 2 to 5 minutes and then removed by suction 10 ml. TBS are added, then removed by suction and the plates again washed with TBS Fresh Dulbecco's modified Eagle medium is subsequently added for all incubation.

One hour after the DMSO shock, 0.1 mmole/liter zinc ions and 0.5 μmole/liter cadmium ions are added thereto for MRE induction. After an incubation period of 6 to 8 hours at 37° C., the concentrations of the metal ions are doubled to an end concentration of 0.2 mmole/liter zinc and 1 μmole/liter cadmium.

For the determination of the transcription activity, the cytoplasmic RNA is isolated 40 to 46 hours after the transfection and determined by S1 nuclease analysis and polyacrylamide gel electrophoresis (Techniques in the Life Sciences, (B5) Nucleic Acid Biochemistry, ed. Flavell (1983), pub. R. A. Elsevier Scientific Publishers Ireland Ltd., pp 1–20). The following Table shows the results obtained. It can be seen that, with the plasmid according to Example 1c, in comparison with the known most active enhancer elements of SV40, there can be obtained a 20 to 30 fold higher transcription activity.

TABLE

| plasmid | relative activity |
| --- | --- |
| 4 × MREwt (Example 1a) | 3 |
| 8 × MREwt (Example 1b) | 3 |
| 4 × MREwt/8 × MREwt (Example 1c) | 20–30 |
| p 1E/SV40 (Example 2) | 1 |

The determination of the activity took place by visual assessment of the X-ray films.

It will be understood that the specification and examples are illustrative but not limitative of the present invention and that other embodiments within the spirit and scope of the invention will suggest themselves to those skilled in the art.

We claim:

1. A eukaryotic expression vector comprising:
   (i) a gene to be expressed,
   (ii) a TATA box,
   (iii) from 3–30 copies of a first nucleotide sequence, wherein said nucleotide sequence in turn comprises from 1–7 copies of a non-viral enhancer sequence motif and is positioned from 1 to 200 base pairs upstream (5') of said TATA box, and
   (iv) from 3 to 30 copies of a second nucleotide sequence, wherein said nucleotide sequence in turn comprises from 1–7 copies of a non-viral enhancer sequence motif of a human gene and is positioned from 1 to 1000 base pairs downstream (3') of said gene.

2. The eukaryotic expression vector of claim 1, wherein said upstream nucleotide sequence is positioned from 8 to 20 base pairs upstream of said TATA box and said downstream nucleotide sequence is positioned from 10 to 300 base pairs downstream of said gene.

3. The eukaryotic expression vector of claim 1, wherein said non-viral enhancer sequence motif is from 8 to 16 base pairs long.

4. The eukaryotic expression vector of claim 1, wherein said upstream nucleotide sequence comprises four copies of the metallothionein enhancer designated MREwt and having nucleotide sequence

5'-GAGCTCTGCACTCCGCCC
    AGACGTGAGGCGGGTCG-5'.

5. The eukaryotic expression vector of claim 1, wherein said downstream second nucleotide sequence comprises eight copies of the metallothionein enhancer designated MREwt and having nucleotide sequence

5'-GAGCTCTGCACTCCGCCC
    AGACGTGAGGCGGGTCG-5'.

6. The eukaryotic expression vector of claim 4, wherein said downstream nucleotide sequence comprises eight copies of the nucleotide sequence of the metallothionein enhancer designated MREwt and having nucleotide sequence

5'-GAGCTCTGCACTCCGCCC
    AGACGTGAGGCGGGTCG-5'.

7. The eukaryotic expression vector of claim 1, wherein said non-viral enhancer sequence motif is the human IgH enhancer sequence motif having nucleotide sequence

TNATTTGCAT.

8. Process for producing a eukaryotic expression vector comprising:
inserting from 3-30 copies of a first nucleotide sequence which in turn comprises from 1-7 copies of a non-viral enhancer sequence motif into a DNA strand which contains a TATA box and a human gene which expresses a protein, wherein said 3-30 copies are inserted from 1-2000 base pairs upstream (5') of said TATA box, and
inserting from 3-30 copies of a second nucleotide sequence which in turn comprises from 1-7 copies of a non-viral enhancer sequence motif of a human gene from 1-1000 base pairs downstream (3') of said human gene.

9. Method for enhanced production of a protein comprising transforming a mammalian host cell with a eukaryotic expression vector, said vector containing (i) a gene which codes for said protein, (ii) a TATA box, (iii) from 3-30 copies of a first nucleotide sequence, wherein said first nucleotide sequence in turn comprises from 1-7 copies of a nucleotide sequence of a non-viral enhancer sequence motif, said 3-30 copies being positioned from 1-200 base pairs upstream (5') of said TATA box, and (iv) from 3-30 copies of a second nucleotide sequence, wherein said second nucleotide sequence in turn comprises from 1-7 copies of a non-viral enhancer sequence motif of a human cell, said 3-30 copies being positioned from 1-1000 base pairs downstream of said gene, and culturing the transformed cell conditions favoring expression of said protein.

* * * * *

UNITED STATES PATENT AND TRADEMARK OFFICE
CERTIFICATE OF CORRECTION

PATENT NO. : 4,983,518
DATED : January 8, 1991
INVENTOR(S) : Walter Schaffner et al.

It is certified that error appears in the above-identified patent and that said Letters Patent is hereby corrected as shown below:

Column 3, line 22: change "GI" to -- GT --.

Signed and Sealed this

Ninth Day of March, 1993

*Attest:*

STEPHEN G. KUNIN

*Attesting Officer*      *Acting Commissioner of Patents and Trademarks*